(12) United States Patent
Bulard et al.

(10) Patent No.: US 7,112,063 B2
(45) Date of Patent: Sep. 26, 2006

(54) DENTAL IMPLANT SYSTEM

(76) Inventors: Ronald A Bulard, Dental Implant Centre, 2401 N. Commerce, Ardmore, OK (US) 73401; Stephen J. Hadwin, 1606 Rosedale, Ardmore, OK (US) 73401

( * ) Notice: Subject to any disclaimer, the term of this patent is extended or adjusted under 35 U.S.C. 154(b) by 0 days.

(21) Appl. No.: 10/916,000

(22) Filed: Aug. 11, 2004

(65) Prior Publication Data
US 2005/0037319 A1  Feb. 17, 2005

Related U.S. Application Data

(60) Provisional application No. 60/493,775, filed on Aug. 11, 2003.

(51) Int. Cl.
*A61C 8/00* (2006.01)
(52) U.S. Cl. .................................... 433/174
(58) Field of Classification Search ............... 433/173, 433/174, 175, 172
See application file for complete search history.

(56) References Cited

U.S. PATENT DOCUMENTS

| | | | |
|---|---|---|---|
| 5,195,892 A * | 3/1993 | Gersberg | 433/174 |
| 5,588,838 A * | 12/1996 | Hansson et al. | 433/173 |
| 5,620,323 A * | 4/1997 | Bressman et al. | 433/174 |
| 5,823,776 A * | 10/1998 | Duerr et al. | 433/173 |
| 6,431,866 B1 * | 8/2002 | Hurson | 433/172 |
| 2004/0121286 A1 | 6/2004 | Aravena et al. | 433/173 |

* cited by examiner

*Primary Examiner*—Melba N. Bumgarner
(74) *Attorney, Agent, or Firm*—Harvey Consulting, P.C.; Derrick Harvey

(57) ABSTRACT

The present invention relates generally to the field of dental implant systems. More specifically, the invention relates to implant anchors with an internal screw portion and an exterior body with threaded and non-threaded portions. Even more specifically, the invention relates to an implant anchor with novel features to prevent leakage between components and vent liquids, compressed air, and biological materials, the implant anchor having a compatibility with a line of implant components.

21 Claims, 9 Drawing Sheets

DENTAL IMPLANT SYSTEM

CROSS-REFERENCE

This application claims cross reference to provisional application No. 60/493,775 filed Aug. 11, 2003.

TECHNICAL FIELD OF THE INVENTION

The present invention relates generally to the field of dental implant systems. More specifically, the invention relates to implant anchors with an internal screw portion and an exterior body with threaded and non-threaded portions. Even more specifically, the invention relates to an implant anchor with novel features to prevent leakage between components and vent liquids, compressed air, and biological materials, the implant anchor having a compatibility with a line of implant components.

BACKGROUND

It is well known in the dental field that for a multi-piece dental implant system to provide exemplary benefits to patients, such a dental implant system must be designed so that its constituent elements interact in a secure and stable manner. Past dental implants systems generally use an initial implant anchors that may take many forms, including blades, subperiosteal, endosseous root-forms, or transitional/ongoing implants. Larger dental implant anchors, generally those 3 mm or more, may require a substantive drilling procedure into the jawbone of a patient. The implant anchors may be designed to work as a foundation for affixing and stabilizing a patient's final prosthetic appliance. Dental implant components may include those that have "press fit," threaded, cylindrical, polygonal fittings and various other types of configurations that are adapted to be mounted to the dental implant anchors. Implant anchors in this particular field encounter issues with long term success, the prevailing indicators of success being stability and reliability.

In past dental implant systems, the relationship between typical sealing interfaces of the implant anchor and the implant component is substantially parallel. That is, regardless of the angle or orientation that the two elements assume relative to a horizontal surface, their relationship to each other is even, or parallel. Theoretically, in the past systems most or all of the interfacing surface area between the implant anchor and implant components makes contact simultaneously. Though the two surfaces may be substantially parallel, on a microscopic level the surfaces can make random initial contact interior of the outer interface perimeter during the seating or assembling process. The past approach of sealing interfaces in a parallel and uniform relationship can have many deleterious effects. First, by initially sealing the interface at non-uniform points interior of the interface perimeter, these past systems may allow gaps or cracks at the outer interface perimeters and throughout the entire interface perimeter as it continues to seal. A non-uniform seal can invite micro-leakage that may cause infectious contamination within the healing portions of the implant site. Next, a non-uniform seal that seals over an entire interface can also create frictional forces that may hinder a practitioner in easily seating the implant component into internal threads of an implant anchor. Finally, the sealing interface of many of the past multi-pieced implant systems is parallel to a plane of the threading motion used to mate implant components to an implant anchor. During a seating process, when the interface seals in a rotational manner in a parallel plane relative to the threading motion of an implant component into an implant anchor, an outside force that affects the plane of the interface seal also affects the security of the implant component that threadably screws into the implant anchor. This arrangement may cause issues with threading security and component stability.

Some multi-piece implant systems have attempted to provide anchor/component interfacing planes that are not parallel to the plane of component threading. For example, interior Morse taper and similar friction-fit configurations have been employed as the interfacing plane between the implant anchor and implant component. An implant anchor/implant component interface using an interior Morse taper, while addressing the issue of a parallel relationship between the plane of interfacing and the plane of threading motion. Some inventions in the art, attempting the address the issues raised herein, envision an abutment with recesses that helps seal against a spherical coronal end of an implant anchor while maintaining s more natural structure of a tooth.

As can be seen, there is a need for a cost effective dental implant reconstruction system. There is a further need for the implant system to prevent the loosening of screwing components and micro-leakage between the implant anchor and the implant component.

SUMMARY OF THE INVENTION

In one embodiment of the invention, An implant anchor, the anchor extending between a basal end placed into bone and a corona, the anchor comprising the following distinct regions:

a) a shaft comprising a non-threaded external and a threaded external portion, the threaded portion disposed between the basal end and the non-threaded portion, the threaded portion comprising a macro-threaded region and a micro-threaded region, the micro-threaded region disposed between the macro-threaded region and the non-threaded portion, the non-threaded portion positioned between the macro-threaded region and the corona of the implant anchor;

b) a non-curved external surface disposed between the non-threaded external portion and the corona;

c) a coronal face located at the corona of the anchor and interior of the non-curved external surface;

d) a mating orifice having distal peaks that breach the non-curved external surface;

e) an internal cavity of the implant anchor, the internal cavity opening at the mating orifice, the internal cavity comprising an anti-rotational mating chamber, a rotational mating chamber, a conduit, and internal threads, the anti-rotational mating chamber and the rotational mating chamber positioned coronally of the internal threads and the mating orifice, the conduit traveling from the internal cavity to the non-curved outer surface;

f) the conduit connecting the non-curved outer surface to the internal cavity.

A second embodiment of the invention relates to combination of the first embodiment and an implant component, the implant component comprising a mating means styled to engage the implant anchor at the mating orifice and to mate with the anchor within the internal cavity, the implant component further comprising a component sealing interface styled to seal onto the implant anchor at the non-curved outer surface, wherein the component sealing interface lies substantially about the same plane. The second embodiment may further comprise an implant component having a) a threaded shaft that screws into the internal threads of the internal cavity of the implant anchor, wherein pressurized fluid, air, and other matter may be vented from the internal cavity via the conduit and the distal peaks of the mating orifice and thus facilitate a more secure fit between the implant anchor and implant component;

b) a component mating means that is cylindrical and mates with the rotational portion of the internal cavity of the implant anchor;

c) more than one piece;

A third embodiment of the invention relates to a dental implant system for securing an implant component onto an implant anchor, the system comprising:

the implant anchor having a corona and a basal end, the anchor comprising:

a) a shaft extending from the basal end, b) a non-curved exterior surface between the shaft and the corona, the non-curved exterior surface having portions defining distal peaks of an anti-rotational mating orifice, the anti-rotational mating orifice extending into an internal cavity;

c) a coronal face at the corona, the coronal face having a rotational mating orifice, the rotational mating orifice extending into an internal cavity;

the implant component having a basal end and a corona, the implant component comprising:

a) a component sealing interface, wherein the non-curved exterior surface and the component sealing interface mechanically seal initially upon a coronal edge of the non-curved exterior surface;

a mating chamber selected from the group of a rotational mating chamber or an anti-rotational mating chamber, the mating chamber engaging at the anti-rotational mating orifice or the rotational mating orifice.

These and other features, aspects and advantages of the present invention will become better understood with reference to the following drawings, description, and claims. For a better understanding of the invention, its operating advantages and the specific aspects of its uses, reference should be made to the accompanying drawings and descriptive matter in which there are illustrated preferred embodiments of the invention. The foregoing has outlined some of the more pertinent aspects of the invention. These aspects should be construed to be merely illustrative of some of the more prominent feature and applications of the present invention. Many other beneficial results can be attained by applying the disclosed invention in a different manner or by modifying the invention within the scope of the disclosure. Accordingly, a fuller understanding of the invention and the detailed description of the preferred embodiments in addition to the scope of the invention are illustrated by the accompanying drawings.

DETAILED DESCRIPTION OF THE INVENTION

The following detailed description shows the best currently contemplated modes of carrying out the invention. The description is not to be taken in a limiting sense, but is made for the purpose of illustrating the general principles of the invention and the best mode for practicing the invention, since the scope of the invention is best defined by the appended claims.

The dental implant system disclosed herein may be used as a conventional, variable staged implant for use in at least three main applications. First, the system may be used in total or partially edentulous mandibles or maxillae. The mandibles and maxillae may have total or partial tooth loss (condition known as edentulous) due to a variety of pathologies. Second, the dental implant system may be used as a terminal or intermediary anchor for a fixed or removeable dental prosthesis of single or multiple units. Third, the implant system may find use in non-dental applications such as for prosthetic attachment components. In each application, the system may be installed in a manner described herein as the placement protocol. The scope of this invention does foresee the possibility that the protocol may be altered when situational environments and applications require such an altered protocol. The commercial embodiment of the inventive dental implant system involves a variable stage implant inserted into an osteotomy site and anchored into a patient's jawbone. The system may include an implant anchor that self-taps into the jawbone. Furthermore, the implant anchor may externally comprise from a coronal end to a basal end a nonthreaded cylindrical portion, a micro-threaded conical portion tapering to a macro-threaded portion. The anchor is designed to receive and interact with associated implant components used in dental implant systems generally known in the arts, the anchor threadably receiving the components in an internal cavity. The internal cavity may comprise an entry end and a securing end. The entry end correlates with a mating orifice at a generally circular coronal face of the implant anchor; the securing end orients axial and opposite of the entry end. Between the entry end and securing end are an anti-rotational mating portion, a rotational mating portion, and internal threads. The anti-rotational mating portion may have an internal hexagonal configuration, mating with a number of associated implant components that interact with the implant anchor in different capacities, including but not limited to seating or unseating the implant anchor in an implantation site, taking impressions of the implant position for prosthetic labwork, to secure a fixed or removeable dental prosthesis, and other applications generally known in art of implantology to require an implant component to be fixed from rotational movement upon the implant anchor. The rotational mating portion may be cylindrical, mating with a number of associated implant components that interact with the implant anchor in different capacities, including but not limited to components that require threading into the internal threads of the implant anchor. These components may include component mating portions that mate with the anti-rotational chamber of the anchor retained by a separate attachment screw. Components may also include female and male mating portions disposed on the end distal of the anchor interface for mating to other components. Because the associated implant components may have, at a microscopic level, a shape that fits onto a coronal edge of the implant anchor in a mechanical sealing interface, the relationship of the interface fit may not be initially even or parallel before or during the seating process. The mating orifice may be located at a coronal face that may taper conically to a cylindrical portion. Though the internal hexagonal configuration may be internal of the anchor face in some embodiments, a preferred embodiment of the invention allows the hexagonal configuration to break out or breach the mating face into the portion that tapers conically. A conduit may connect the internal cavity with the non-curved exterior surface, the conduit extending between two conduit ports, one located in the internal cavity distally of the mating orifice and the other within the non-curved exterior surface of the implant.

The dental implant and implant component system envisioned by the present invention differs greatly both in function and in structure from past attempts to create secure, sealed and reliable implant systems. The present invention provides the novel advantage of mechanically sealing an implant component to a coronal edge of a non-curved surface of the anchor through offsetting the component and implant anchor. Because the interface seals down initially at the coronal edge of the non-curved surface and then inward, the present invention provides the component with a substantially axial force. Such a force would push the implant component away from the implant anchor. Thus, this force aids in "locking" a threaded component into place for a more stable and secure seal. The invention further provides the advantage of allowing the component to gradually engage more surface area of the implant anchor as the component seats upon the anchor from the outer coronal edge inward, assuring that leaks and gaps do not occur. The invention also provides an advantageous means to vent pressure from an implant anchor's cavity through a novel placement of a conduit. During the seating or assembling process of an implant component onto an implant anchor, a threaded component threadably displaces air, fluid, and biological materials first through internal threads of the implant component, and then through a cylindrical portion of the internal cavity. Pressure may build as trapped air compresses between the sealing component and anchor. The present inventive implant may release the compressed trapped air via the conduit, and to a lesser extent, protruding points of the internal hex that break out of the cylindrical portion of the internal cavity. The release of this pressurized air, liquid, and biological material provides a novel advantage of a tighter seal between the implant components and implant anchor. A tighter seal ensures better compatibility and stability between the components and the implant anchor, resulting ultimately in the ability of the present implant system to support more immediate and powerful lateral, anterior, and posterior forces upon the implant system. Finally, the conduit was discovered to provide an unexpected benefit in the form of a locking mechanism. During seating of a threaded component into the internal threads of the implant anchor, as the implant anchor and implant component seal at the interface the section of the implant component that interfaces and corresponds with the conduit port is drawn into the conduit through an inverse pressure gradient. This adds yet another assurance of security that the component will not move from its seated position relative to the anchor. Any further advantages will be apparent as aspects of the invention are described in detail.

Surgical Protocol

The inventive implant system comprises the implant anchor and associated implant components. The most common application of the implant system is for dental implantation, or implant dentistry. The inventive system has a recommended surgical protocol for optimal placing of the implant system, beginning with the implantation of the implant anchor. The first step of the surgical protocol involves preparing the implant anchor site by clearing the soft tissue from the future osteotomy site. A dental practitioner may initially drill an osteotomy site at a location of interest, using a series of irrigated drills. Stylized drills resemble the dimensions of an unthreaded implant anchor may be used to bore an osteotomy site. Another aspect of the invention foresees using such stylized drills to drill consecutively larger osteotomy site diameters until the diameter of the site of the implant anchor's unthreaded shaft is achieved. For example, a practitioner implanting a 3.5 mm implant (not including thread diameter) may first use a locator drill, a 2.0 mm drill, a 3.5 mm drill, and then a counterbore for a drilling technique that minimizes trauma and maximizes the success a practitioner has in drilling smooth, straight osteotomy sites, even in dense bone. The practitioner may additionally use a larger drill when the implant size calls for such, as in a 4.3 mm drill for a 4.3 mm shaft diameter implant anchor. The counterbore may be employed to bore a tapered portion of the osteotomy site correlating to the coronal end of the implant. A bone tap may be utilized to finalize osteotomy site. A bone tap that correlates to the dimensions and threading of the implant anchor may be used in adversely dense bone sites so that the bone tap threads the bone within and bordering the drilled osteotomy site to ensure that the threads of the implant anchor screw easier into the bone.

The second step of the surgical protocol involves the insertion of the implant anchor into the osteotomy site. The implant anchor may be delivered to the practitioner in a vial. The vial may comprise a sterile implant anchor that is secured to a vial cap, whereas the implant anchor does not touch the vial. The practitioner may remove the vial cap and secured implant anchor from the vial and insert the implant anchor directly into the osteotormy site, ensuring the sterility of the implant until placed in a patient's osteotomy site. The practitioner may then turn the vial cap to begin seating the implant into the bone threaded by the bone tap until the anchor is stabilized. At this point, the practitioner has least three options for finally seating the implant anchor into the osteotomy site. One option is to use an implant finger driver. An implant finger driver comprises a manual engagement portion atop the finger driver and a mating portion at the bottom of the finger driver so that a practitioner may manually turn the finger driver and tactically sense when the implant anchor has finally seated into the osteotomy site. The mating portion correlates to a mating orifice of the implant anchor. An apical tip of mating portion may mate with an orifice in some prosthetic components. A second option is to use an implant latch driver to finally set the implant. The implant latch driver comprises an engagement portion and a mating portion, the engagement portion being engaged into a latch-type handpiece. The mating portion correlates to a mating orifice of the implant anchor. A third option to finally seat the implant anchor is the ratchet driver that fits into a ratchet wrench or a pre-calibrated torque wrench. A ratchet driver comprises an engagement portion and a mating portion. The configuration of the mating orifice of the implant anchor may be consistent with that of the mating portion of each of the drivers. If the mating orifice is an internal hex, then the mating portion of each of the drivers will have a hex driver that mates and engages the mating orifice.

The third and final step of the surgical protocol is the healing phase. The healing phase comprises placing a healing screw atop the fully and finally seated implant anchor. The cover screw comprises a mating portion that fully threads in an internal threaded portion of the implant anchor and seats upon a non-curved exterior surface of the implant anchor. The cover screw further comprises an engagement portion atop the screw that allows engagement by the finger, latch, and ratchet drivers. The engagement portion of the cover screw allows a practitioner to engage the cover screw and drive it into the internal threaded portion of the implant anchor.

Figure 1:
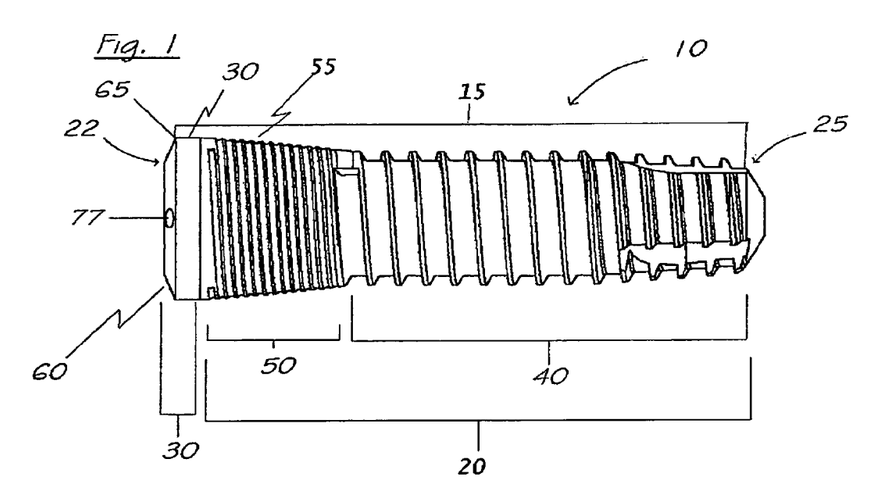
FIG. 1 is a side view of the implant.

Looking at an embodiment of the invention shown in FIG. 1, an implant anchor 10 is shown to have a shaft 15 comprising a threaded portion 20 extending from a basal end 25. Shaft 15 may comprise a non-threaded portion 30 at a coronal 22. Threaded portion 20 may conically flare and comprise a macro-threaded portion 40 and micro-threaded portion 50, the macro-threaded portion 40 being more proximal to the basal end 25 than the micro-threaded portion 50. Micro-threaded portion 50 has threads 55 styled to preserve cortical bone at the crestal ridge by reducing bone stress and axial stiffness. The threads 55 of micro-threaded portion 50 may be triple-threaded to avoid stripping the groove cut by macro-threaded portion 40. The triple threading of micro-threaded portion 50 functionally operates by compacting rather than cutting the bone.

The threading discussed above and the implant body disclosed is a best mode and may be changed without altering the scope of the present invention. Any implant anchor body generally known in the arts may be used without departing from the invention, including a non-threaded anchor or an anchor with non-threaded portions, an anchor comprising a perpendicular hole or bore therethrough, a non-tapering anchor, an anchor with convex and/or concave sections, or a press fit anchor.

Figure 2A:
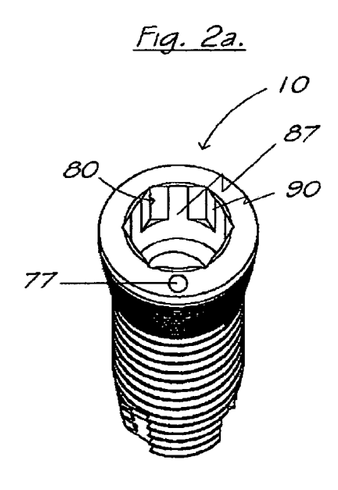
FIG. 2a is coronal side perspective view of the implant.
Figure 2B:
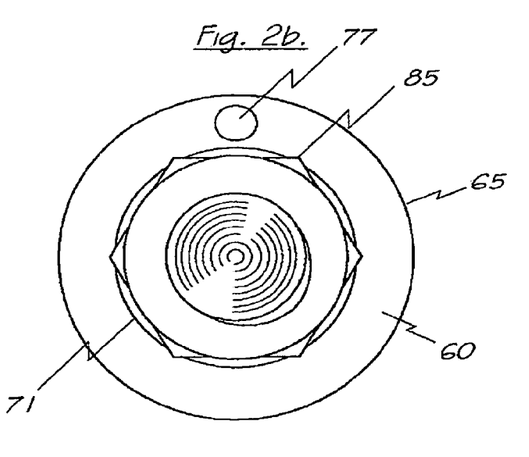
FIG. 2b is axial cross-sectional from a coronal view of the top of the implant.
Figures 3A, 3B:
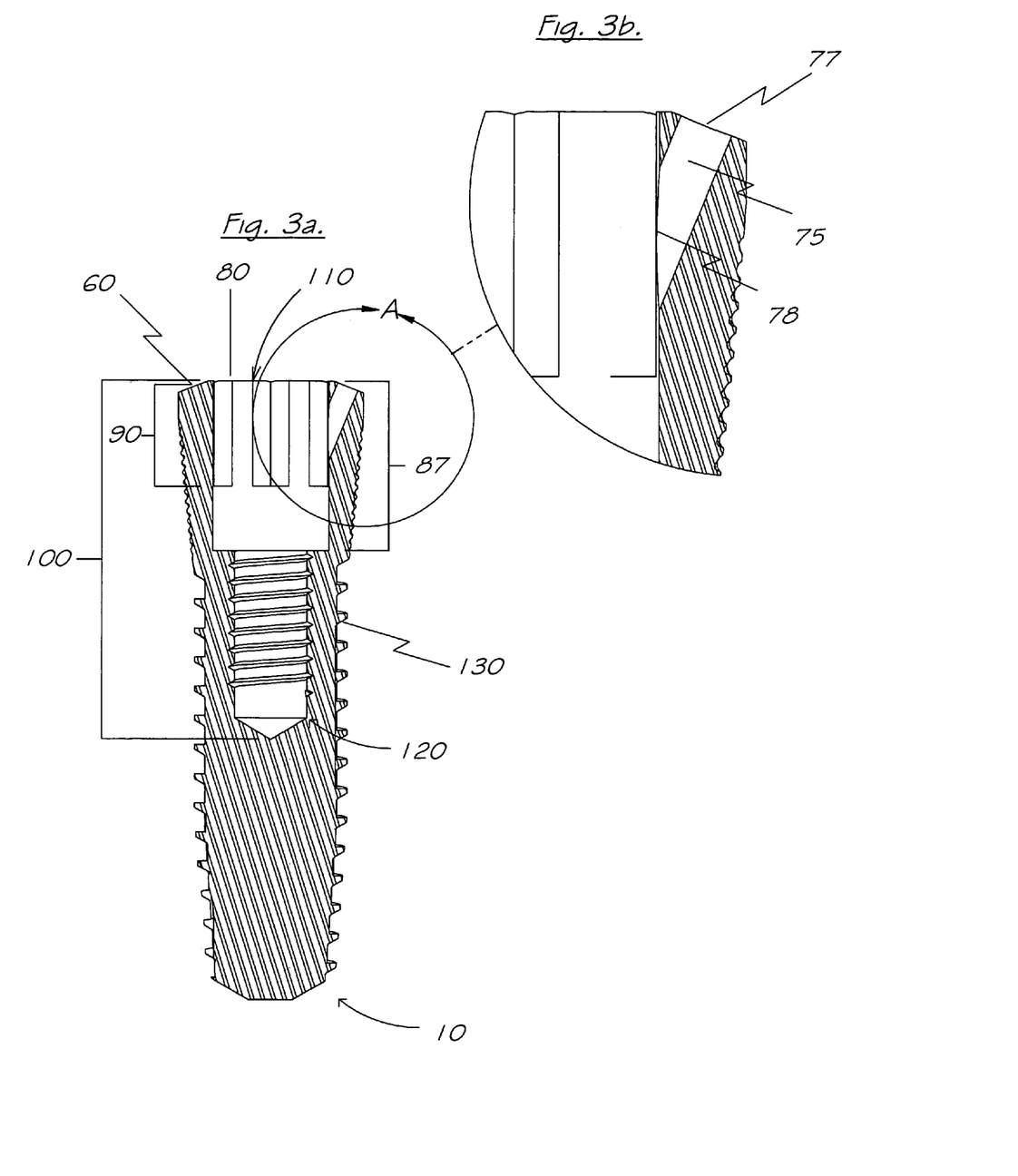
FIG. 3a shows a transversal cross-sectional view of the implant.
FIG. 3b shows a perspective side view of the cover screw.

Looking at FIGS. 1–3, non-threaded portion 30 may comprise a cylindrical outer surface (not shown). Continuing toward the coronal 22, a non-curved external surface 60 may be disposed between the outer surface of the non-threaded portion 30 and the coronal 22. A mating orifice 80 may be located at a coronal face 71 of the coronal 22. The mating orifice 80 is styled to receive a variety of components that mate with the implant anchor 10, the orifice 80 to receive components of at least two different mating means. Cylindrical outer surface of non-threaded portion 30, which may be positioned between the micro-threaded portion 50 and the non-curved external surface 60, affords the implant practitioner options in determining the implant anchor's 10 vertical depth during the implantation process. Outer surface of non-threaded portion 30 in a preferred embodiment may be a smooth surface so that gingival tissue is not irritated or aggravated. Non-curved external surface 60 may taper from the cylindrical outer surface of the non-threaded portion 30 to the coronal face 71, and in some embodiments comprise levels of non-curved surfaces, or multiple faces, separated by sloped margin (not shown). In another embodiment of the invention, a sloped margin may separate the non-curved external surface 60 from outer surface of the non-threaded portion 30, the sloped margin.

Looking now to FIGS. 2a–3b, an internal cavity 100 may extend between an entry end 110 and a securing end 120. The entry end 110 is located at the corona 22 of the implant anchor 10, and comprises the mating orifice 80 that breaks out of the coronal face 71; the securing end 120 is disposed axial and opposite of the entry end 110. The distal peaks 85 of the mating orifice 80 between the entry end 110 and securing end 120 are the mating orifice 80, an anti-rotational mating chamber 90, a rotational mating chamber 87, and an internal threaded portion 130. The mating orifice 80 may comprise one or more internal flats 92 that together form the anti-rotational mating chamber 90. The intersection of the internal flats 92, extending coronally, are seen externally as the distal peaks 85 of the mating orifice 80, and may engage at least a portion of associated implant components during the component interactions and matings with the implant anchor 10. Anti-rotational mating chamber 90 occupies common space with a rotational mating chamber 87, but comprises the distal peaks 85 of the mating orifice 80 that extend outside the rotational mating chamber 87. The concept of the anti-rotational mating chamber 90 being greater than the rotational mating chamber portion 87 provides the aforementioned benefit of venting while a rotational mating portion of a component threadably screws into the internal threaded portion 130 of the internal cavity 100. In other embodiments within the scope of the invention, mating orifice 80 may also taper or bevel.

Non-curved external surface 60 may open into a conduit 75 via a conduit port 77 within the non-curved external surface 60. In one especially preferred embodiment of the invention, conduit 75 comprises ports 77, 78, the conduit extending from the port 77 at non-curved external surface 60 to port 78 communicating with the internal cavity 100 of the implant anchor 10. The path that conduit 75 may travel from the non-curved external surface 60 to the internal cavity 100 is one diagonal to a vertical axis 79 (not shown) of the implant anchor 10. Other configurations of conduit 75 are envisioned by the current invention, including those that aid in the locking function of the conduit, such as irregular, asymmetric or nonlinear stylings. Conduit 75 vents pressure caused by biological materials, fluid, and gas displaced from the internal cavity 100 when a user seats or assembles associated components to a final torque. The conduit port 77 may be disposed anywhere interior of a coronal edge of the non-curved exterior surface 60. Conduit port 78 may be disposed anywhere in the internal cavity 100. In one embodiment, conduit port 78 may be disposed above the seating portion of a rotational mating portion 87 of the internal cavity 100. In other words, port 78 may be disposed between the seating portion of rotational mating portion 87 and the entry end 110 of the internal cavity 100. Looking at FIG. 4b, a preferred embodiment shows implant component 200 sealing onto implant anchor 10 from the coronal edge 65 of the implant anchor 10 proximal, or inward. This "outside-to-inside" sealing allows the conduit 75 to remain open and transmit the pressurized air, liquid, and/or biological materials for a substantial amount of the interface sealing. The unexpected benefit of conduit 75 facilitating a tighter relationship between the implant anchor 10 and its associated mating component occurs for two reasons. First, the conduit 75 relieves the internal cavity 100 of pressure that would otherwise counteract the seating between the anchor 10 and the mating component. Second, an unexpected benefit of positioning conduit port 77 on the non-curved external surface 60 was discovered to advantageously lock the implant anchor 10 onto its associated implant mating component 200 for better implant system stability. As the associated implant component 200 tightens and mates with the implant anchor 10, the implant component 200 seals upon the implant coronal face 71 and the non-curved external surface 60. This results in an extrusion of the implant component 200 into conduit 75 via conduit port 77. The extrusion of the component into the conduit port 77 and conduit 75 locks the implant component 200 into the conduit 75 of the implant anchor 10.

Coronal face 71 may be configured in a circular style, though other configurations with rounded, n-gonal, convex, or concave perimeters may be used. In a preferred embodiment, coronal face 71 may have dimensions not exceeding 0.116 mm, though other embodiments may have other dimensions. Coronal face 71 may comprise a rotational mating portion 87 of the mating orifice 80. In one embodiment of the invention, mating orifice 80 may be of a hexagonal configuration, though the scope of the invention foresees alternative embodiments of the mating orifice that may include any symmetric, asymmetric, irregular, circular (such as elliptical or broken parabolic), spline (including involute) or other configurations not named but known in the arts. Looking at a top view of the implant in FIG. 2b, distal peaks 85 of the mating orifice 80 may break out of or breach the distal perimeter 95 of the coronal face 71 into the non-curved external surface 60. The concept of having the hexagonal configuration or generally any mating orifice 80 configuration break out of or breach the coronal face 71 into the non-curved external surface 60 yielded an unexpected benefit of additional venting of pressure above the conduit 75 in the internal cavity 100 during the seating or assembling process for reasons described hereafter.

In embodiments of the invention exemplified in FIGS. 5–12, implant components 200 are shown that are capable of mating with implant anchor 10. These styles of components are used for exemplary reasons and not as a limitation of the types of components that mate with implant anchor 10. The examples of implant components 200 are not limited to cover screws, posts, waxing cylinders, coping cylinders and other types of abutments. A preferred embodiment of this invention further envisions any implant component 200 having mating interfaces that mate and interface, and seal onto implant anchor 10. In this preferred embodiment, implant anchor 10 may be configured in varied lengths and diameters and yet retain a standard interface size. Thus, implant anchor 10 may comprise variations in the size of its threaded portion 20 and non-threaded portion 30, the variations tailored for different size requirements of the user. This approach encompasses an inventive step over many past systems, which required different sizes of components for different sized-anchors.

Figure 4A:
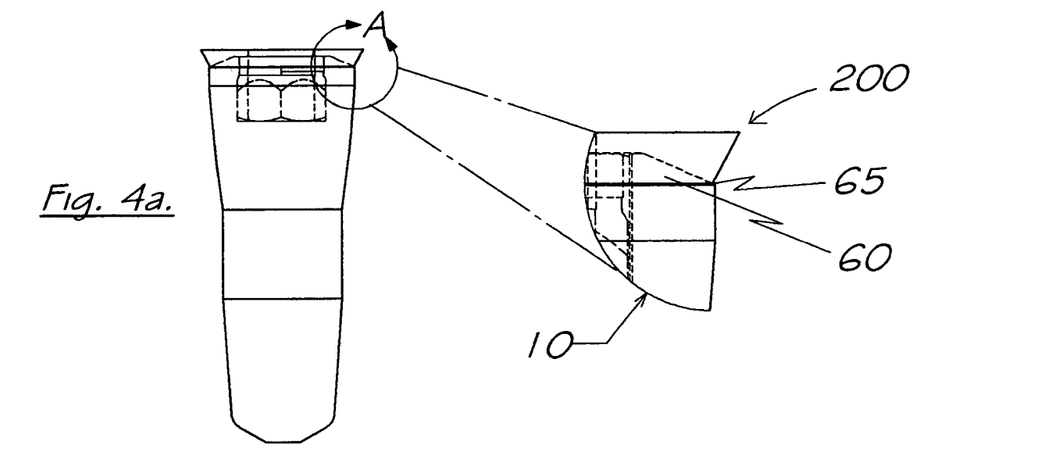
FIGS. 4a–4c show side interior views of the implant and implant component interface.
Figure 4B:
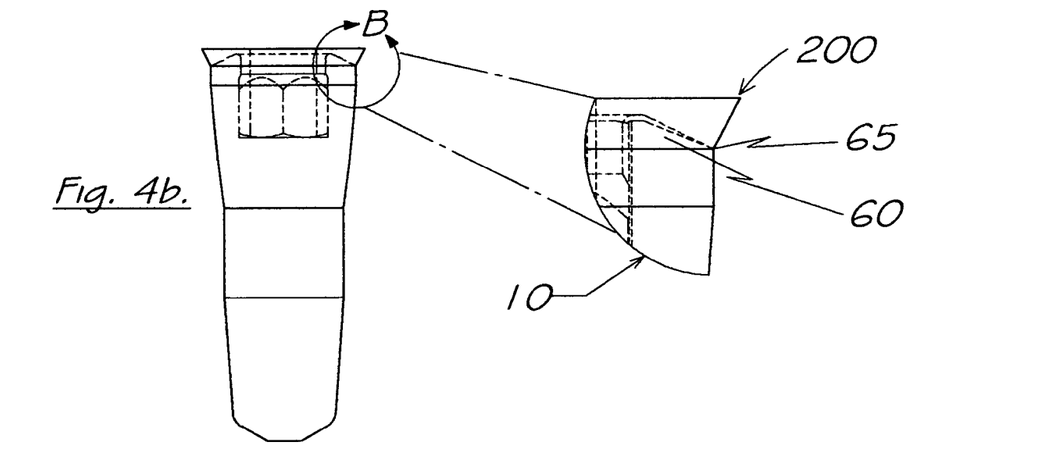
Figure 4C:
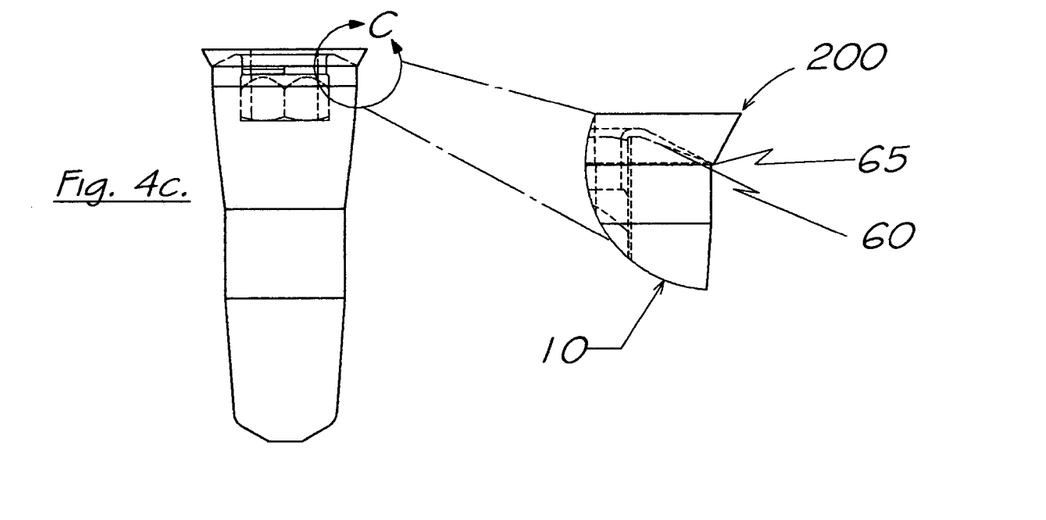
Figures 5A, 5B:
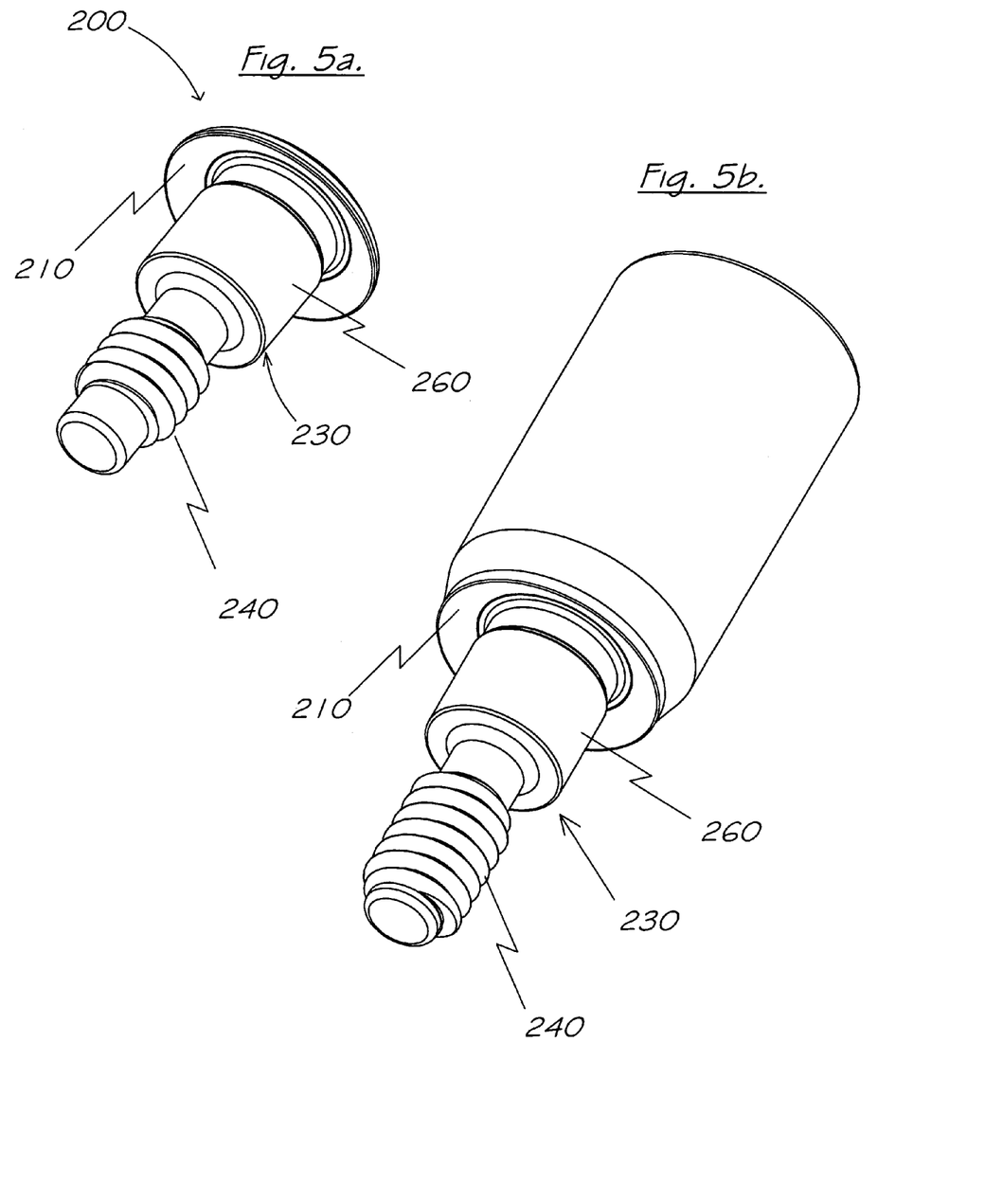
FIGS. 5a and 5b show basal perspective views of implant components
Figures 6A, 6B:
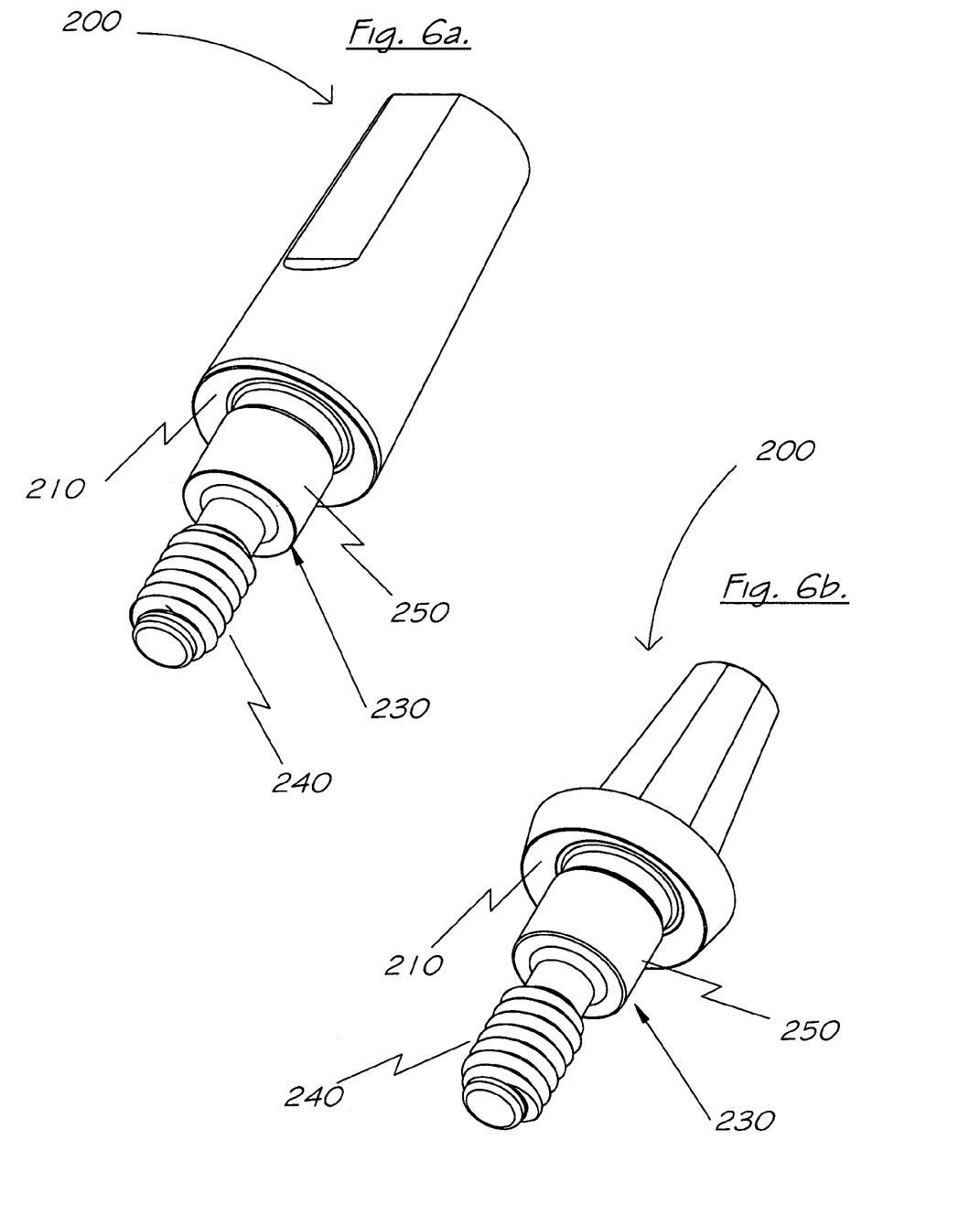
FIGS. 6a and 6b show associated implant components.
Figure 7A:
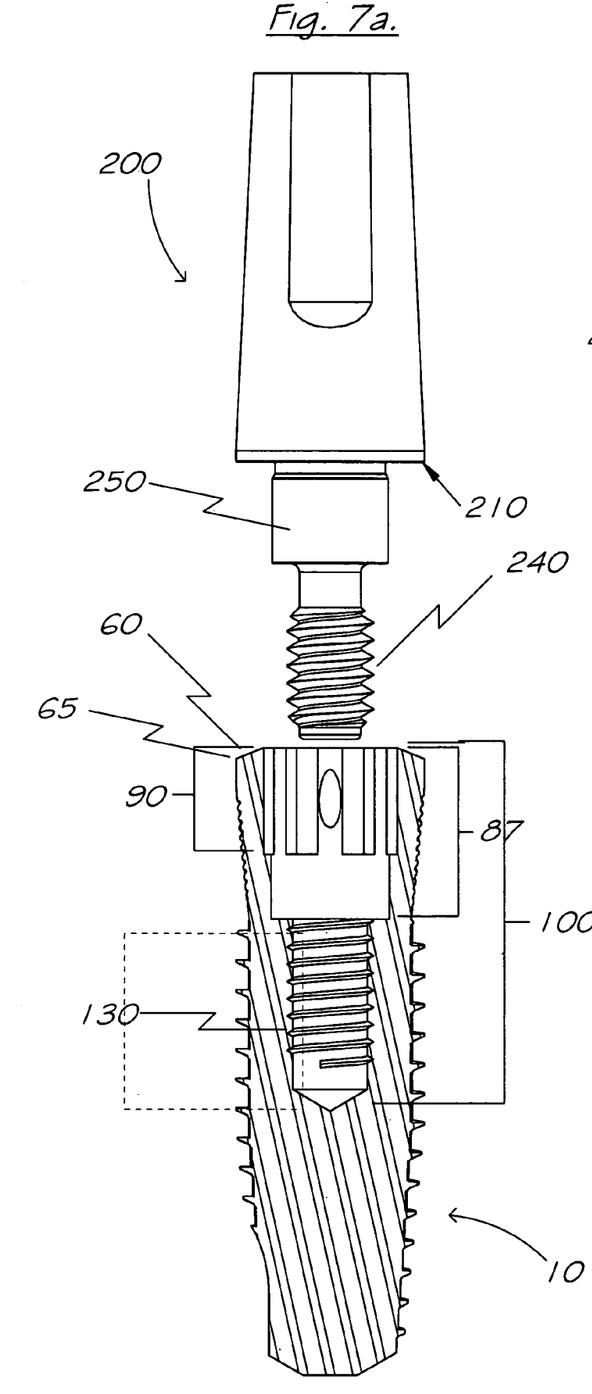
FIGS. 7a shows a side interior view of an implant anchor and with an associated implant component before mating and seating.
Figure 7B:
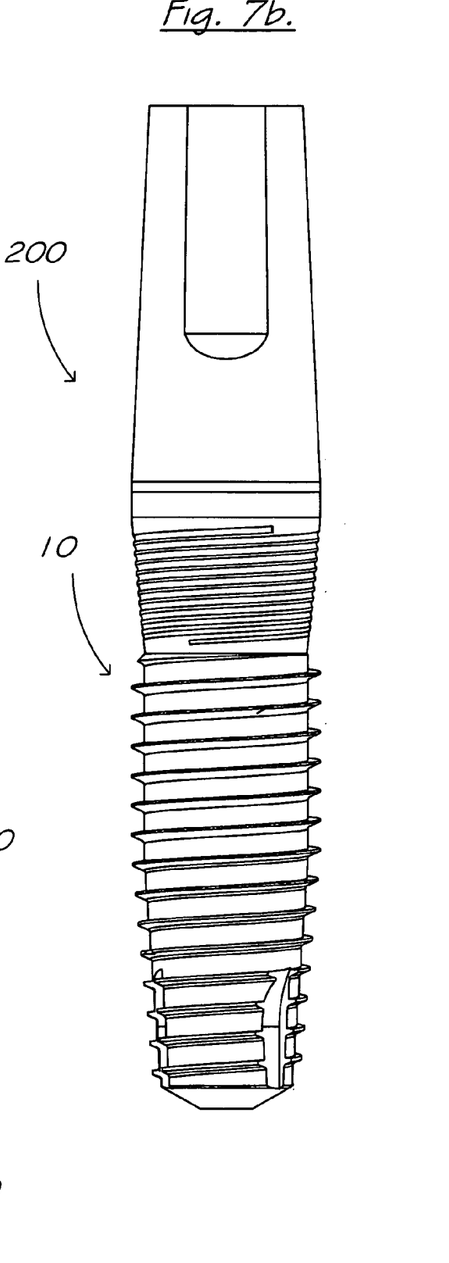
FIG. 7b shows a side view of an implant component mated and seated upon and into an implant anchor.

Looking now at preferred embodiments shown in FIGS. 4a–4c, the implant anchor 10 with the non-curved external surface 60 will have the implant component 200 that interfaces with the implant anchor 10 in a mechanical sealing interface, the interface occurring initially at a coronal edge 65 of the non-curved external surface 60 of the implant anchor 10. Though the associated mating components such as implant components 200 shown have the mechanical sealing interface that fits atop the implant anchor 10, the relationship of the interface fit is not initially even. Even with small tolerance deviations that are acceptable within the medical device industry, the present invention accomplishes its objective of sealing the implant component 200 upon the coronal edge 65 of the non-curved external surface 60 of the implant anchor 10. FIG. 4a illustrates that the interface fit may appear even after coincidental sealing of the entire interface. FIG. 4b exhibits a scenario in which the implant 10 is at its maximum permissive limit. FIG. 4c shows a scenario of the implant component 200 at its maximum permissive limit. During the seating or assembling process, marginal portions of the perimeter of the implant anchor 10 and component sealing interface 210 may communicate and seal before the more interior portion of the anchor and component interface communicate and seal. That is, the component sealing interface's 210 relationship with the non-curved external surface 60 of the anchor may resemble a slightly acute angle, or a mechanical sealing interface. The result is that the perimeter of the implant anchor 10 and component sealing interface 210 seals first during the seating or assembling process (when the implant component 200 threads into the internal threaded portion 130 of the anchor), thus having at least two advantageous effects. First, potentially infectious materials from outside the interface cannot seep into perimeter of the interface. Second, the mechanical sealing interface described herein reduces the contact surface area between the implant anchor 10 and implant component 200 during the seating or assembling process. The reduced contact surface area allows the implant component 200 to plasticize contiguously to the implant anchor 10 from its coronal edge 65 inwardly as the implant component 200 tightens. The pull-out force of the implant component 200 is also reduced for two reasons. First, less force or torque is required to seat the implant component 200 because of the reduced surface area and thus reduced frictional force. Second, the tensile memory of the implant component 200 allows it to return to its original shape after being plasticized, using less force.

Figures 8A, 8B:
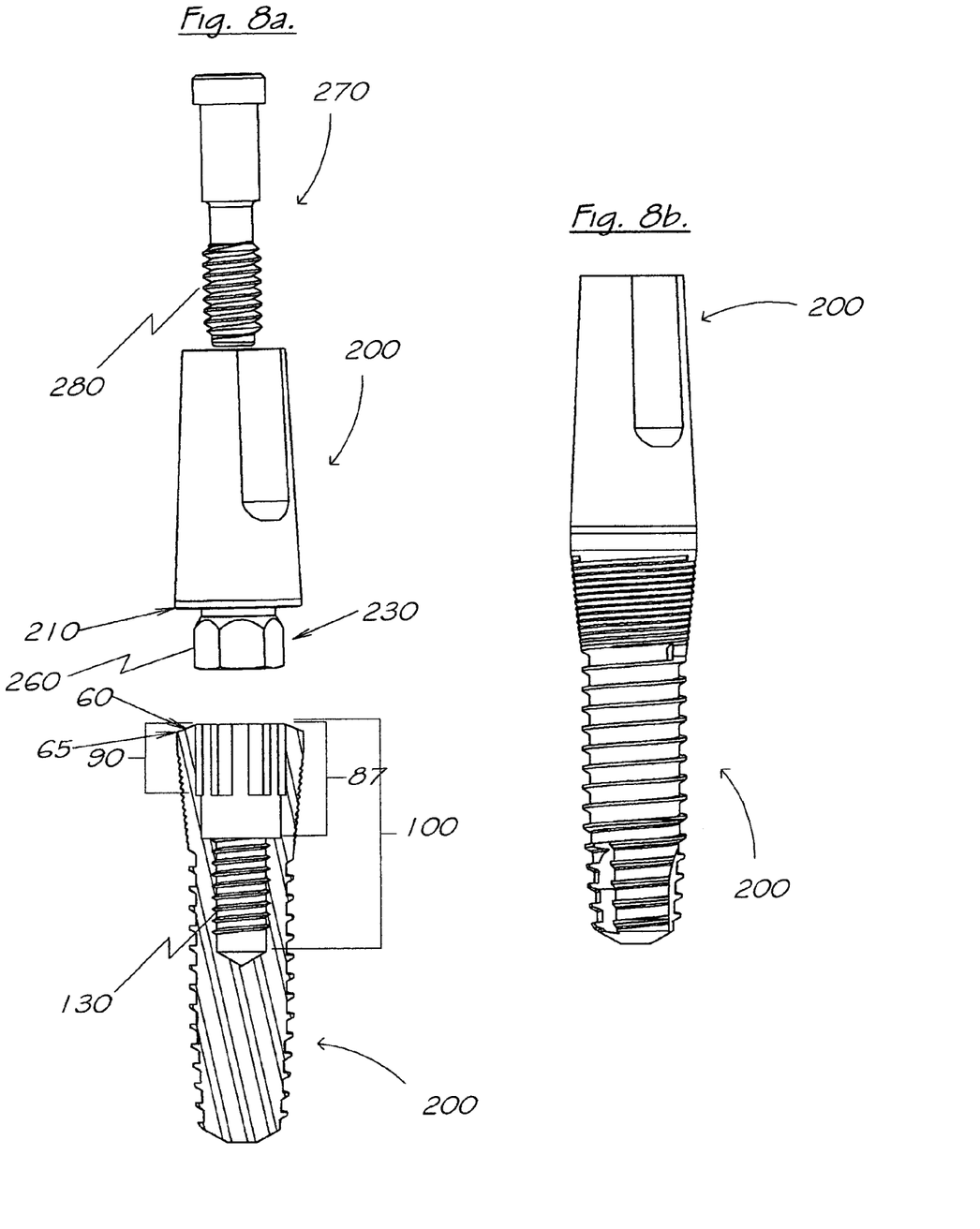
FIG. 8a shows a side interior view of an implant anchor and with associated implant components before mating and seating
FIG. 8b shows a side view of an implant component mated and seated upon and into an implant anchor.
Figures 9, 10:
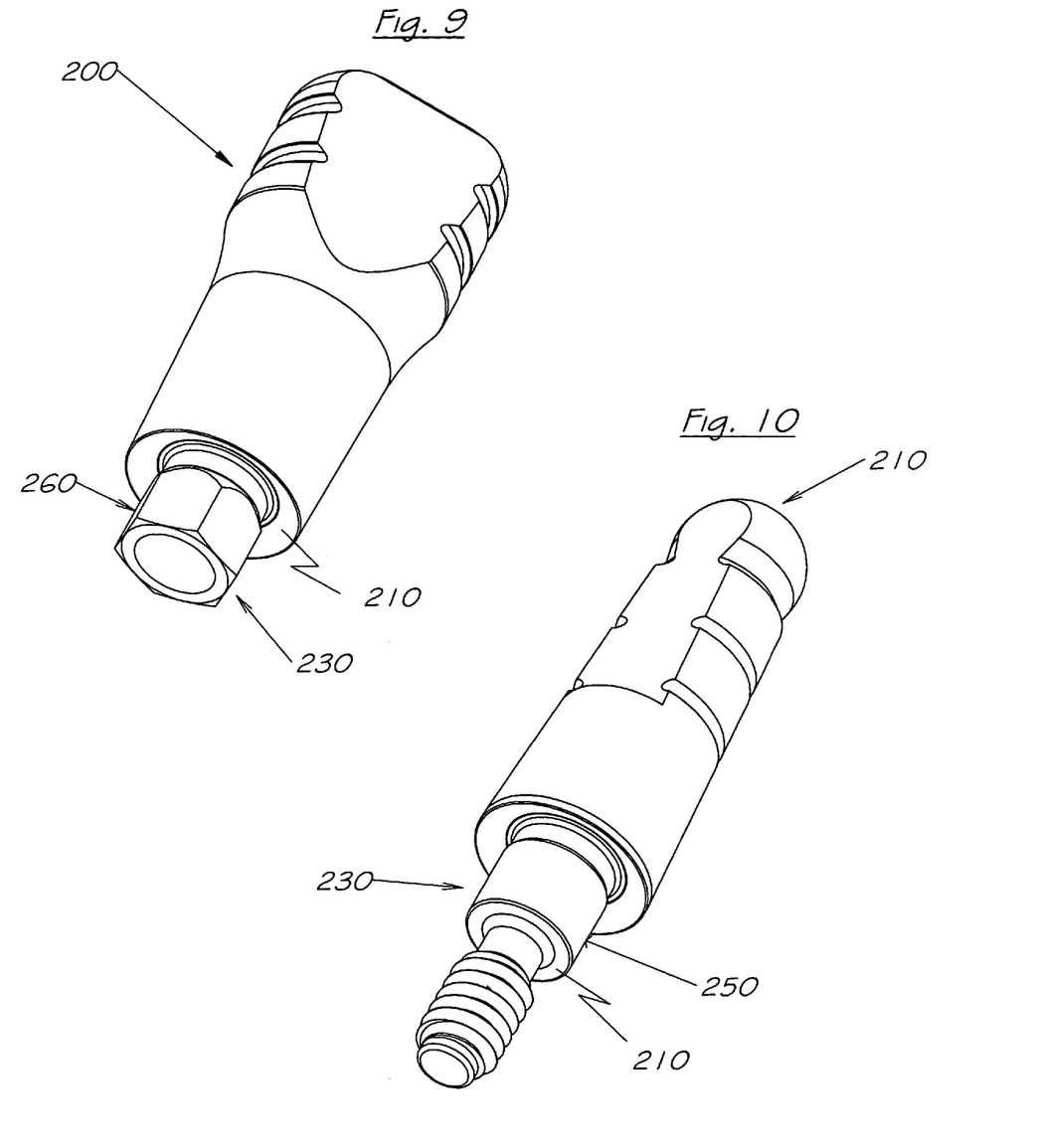
FIG. 9 shows a basal side perspective view of an associated implant component.
FIG. 10 shows a basal side perspective view of an associated implant component.
Figures 11, 12:
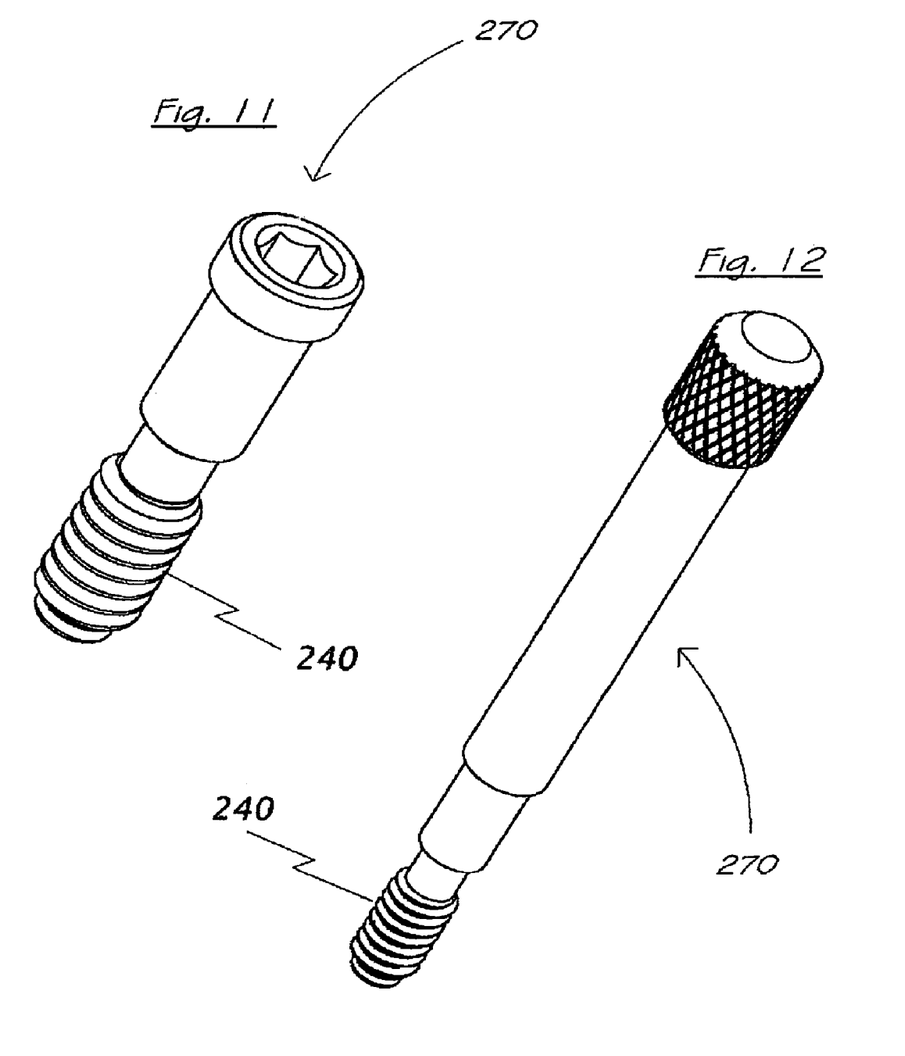
FIG. 11 shows a coronal side perspective view of an associated implant component.
FIG. 12 shows a coronal side perspective view of an associated implant component.

In operation, many scenarios may materialize for a practitioner utilizing the inventive implant system. The system is designed to support components of dental implants from mating the implant component 200 that may screw into internal threads 150 at the securing end 120 of the internal cavity 100 of the implant anchor 10, engage at the mating orifice 80, and lock at the conduit 75 and specifically conduit port 77. Implant anchor 10 can support implant components 200 that have female and male mating portions that are rotational 250 or anti-rotational 260. FIGS. 5a–12 exhibit examples of different types of implant components 200 that this inventive system envisions; however, the group of components shown should not be an exhaustive or limiting list. Thus, any component known to those having skill in the art of dental implantology may be used in this system if those elements comprise mating portions and a sealing interface that mates and seals with the implant anchor 10. Looking at FIGS. 5a–12 the implant component 200 may comprise a component mating means 230 with a width that mates with the rotational mating chamber 87 or the anti-rotational mating chamber 90 of the mating orifice 80 that extends into the internal cavity 100 of the implant anchor 10. Component threads 240 may thread into the internal threaded portion 130 of the implant anchor 10. In a multi-piece component assembly 270, as seen in FIG. 8a, the assembly component thread 240 may be employed to screw into the internal Threaded portion 130 of the implant anchor 10.

The present invention may be forged with any material generally known in the art of implants to carry out its objectives of security and reliability. In a preferred embodiment, titanium or a titanium alloy may be used in the implant and components to increase elasticity and memory, especially in the interface regions.

The present invention may also be embodied, for best mode and commercial use purposes (and not for purposes of limitation, as the implant system may be practiced with any dimensional range) in the following dimensions for respective structural elements. Internal flats 92 may have a width no greater than 0.104 inches and a depth of no more than 0.085 inches, the rotational mating chamber 87 may have a diameter of no more than 0.106 inches and a depth of 0.15 inches or greater, coronal face 71 may have a diameter of 0.116 inches, and an angle of the non-curved external surface 60 from the non-threaded portion 30 to the coronal face 71 is between 20 to 24 degrees. The preceding dimensions describe one preferred, embodiment.

As has been demonstrated, the present invention provides advantageous techniques for a dental implant system that provides an implant anchor with features providing more secure mating with implant components also styled according to the invention. While the preferred embodiments of the present invention have been described, additional variations and modifications in those embodiments may occur to those skilled in the art once they learn of the basic inventive concepts. Therefore, it is intended that the appended claims shall be construed to include both the preferred embodiment and all such variations and modifications as fall within the spirit and scope of the invention.

We claim:

1. An implant anchor, the anchor extending between a basal end placed into bone and a corona, the anchor comprising the following distinct regions:
    a shaft comprising a non-threaded portion and a threaded portion, the threaded portion disposed between the basal end and the non-threaded portion, the threaded portion comprising a macro-threaded portion and a micro-threaded portion, the micro-threaded portion disposed between the macro-threaded portion and the non-threaded portion, the non-threaded portion positioned between the macro-threaded portion and the corona of the implant anchor;
    a non-curved external surface disposed between the non-threaded portion and the corona;
    a coronal face located at the corona of the anchor and interior of the non-curved external surface;
    a mating orifice having distal peaks that breach the non-curved external surface;
    an internal cavity of the implant anchor, the internal cavity opening at the mating orifice, the internal cavity comprising an anti-rotational mating chamber, a rotational mating chamber, a conduit, and internal threads, the anti-rotational mating chamber and the rotational mating chamber positioned coronally of the internal threads and the mating orifice, the conduit traveling from the internal cavity to the non-curved external surface; and
    the conduit connecting the non-curved external surface to the internal cavity.

2. A combination implant anchor and implant component system, the system comprising:
    the implant anchor described in claim 1; and
    at least one implant component comprising a mating means styled to engage the implant anchor at the mating orifice and to mate with the anchor within the internal cavity, the implant component further comprising a component sealing interface styled to seal onto the implant anchor at the non-curved external surface.

3. The combination implant anchor and implant component system in claim 2, the implant component further comprising
    a threaded shaft that screws into the internal threads of the internal cavity of the implant anchor, wherein pressurized fluid, air, and other matter may be vented from the internal cavity through the conduit at the non-curved external surface and through the distal peaks of the mating orifice, thus facilitating a more secure fit between the implant anchor and implant component.

4. The combination implant anchor and implant component system in claim 3, the implant component further comprising more than one piece.

5. The combination implant anchor and implant component system in claim 2, wherein the component mating means is cylindrical and mates with the rotational mating chamber of the internal cavity of the implant anchor.

6. The combination implant anchor and implant component system in claim 2, the anti-rotational mating chamber of the implant anchor resembling a hexagonal configuration.

7. The combination implant anchor and implant component system in claim 2, the rotational mating chamber of the internal cavity resembling a cylindrical configurations.

8. The combination implant anchor and implant component system in claim 2, the coronal face being substantially perpendicular to the non-threaded portion of the shaft.

9. The combination implant anchor and implant component system in claim 2, wherein the implant component is a temporary abutment.

10. The combination implant anchor and implant component system in claim 2, wherein the implant component is a permanent abutment.

11. The combination implant anchor and implant component system in claim 2, the anti-rotational mating chamber further comprising internal flats having a width of no more than 0.104 inches and a depth of no more than 0.085 inches.

12. A dental implant system for securing an implant component onto an implant anchor, the system comprising:
    the implant anchor having a corona and a basal end, the anchor comprising;
        a) a shaft extending from the basal end,
        b) a non-curved external surface between the shaft and the corona, the non-curved external surface having portions defined by distal peaks of an anti-rotational mating orifice;
        c) an internal cavity of the implant anchor having internal threads, the anti-rotational mating orifice extending into the internal cavity;
        d) an coronal face at the corona, the coronal face having a rotational mating orifice, the rotational mating orifice extending into the internal cavity; and
    the implant component comprising:
        a) a component sealing interface, wherein the non-curved external surface and the component sealing interface seal upon a coronal edge of the non-curved external surface; and
        b) a threaded shaft that screws into the internal threads of the internal cavity of the implant anchor during seating of the implant component onto the implant anchor, whereby the component sealing interface mechanically seals from the coronal edge inward, applying an axial and coronal force to the component that locks the threaded shaft into the internal threads of the internal cavity.

13. The dental implant system in claim 12, the anchor comprising a conduit having conduit ports at the internal cavity and the non-curved external surface, whereby the conduit vents pressurized gas, liquid, and biological material as the component sealing interface mechanically seals from the coronal edge inward.

14. The implant anchor in claim 12, the coronal face being substantially perpendicular to the shaft.

15. The dental implant system in claim 12, the anti-rotational mating orifice of the implant anchor resembling a hexagonal configuration.

16. The dental implant system in claim 12, the rotational mating orifice of the internal cavity resembling a cylindrical configuration.

17. The dental implant system in claim 16, the implant component further comprising more than one piece.

18. The dental implant system in claim 12, the coronal face being substantially perpendicular to the shaft.

19. The dental implant system in claim 12, wherein the implant component is a temporary abutment.

20. The dental implant system in claim 12, wherein the implant component is a permanent abutment.

21. The dental implant system in claim 12, the anti-rotational mating orifice further comprising internal flats having a width of no more than 0.104 inches and a depth of no more than 0.085 inches.

* * * * *